United States Patent
Sharma et al.

(10) Patent No.: US 8,597,617 B2
(45) Date of Patent: Dec. 3, 2013

(54) COATED NATURAL CALCIUM CARBONATE ORAL CARE TOOTHPOWDER COMPOSITION

(75) Inventors: Nina Sharma, Mumbai (IN); Ramesh Nair, Pune (IN)

(73) Assignee: Colgate-Palmolive Company, New York, NY (US)

( * ) Notice: Subject to any disclaimer, the term of this patent is extended or adjusted under 35 U.S.C. 154(b) by 2960 days.

(21) Appl. No.: 11/020,016

(22) Filed: Dec. 21, 2004

(65) Prior Publication Data

US 2006/0134013 A1 Jun. 22, 2006

(51) Int. Cl.
*A61K 8/00* (2006.01)

(52) U.S. Cl.
USPC .......................................................... 424/49

(58) Field of Classification Search
USPC .......................................................... 424/52
See application file for complete search history.

(56) References Cited

U.S. PATENT DOCUMENTS

| | | | |
|---|---|---|---|
| 4,423,030 A | 12/1983 | Hayes et al. | |
| 4,512,741 A | 4/1985 | Mushta | |
| 4,855,128 A * | 8/1989 | Lynch et al. | 424/49 |
| 4,960,597 A | 10/1990 | Farbood et al. | |
| 5,182,101 A | 1/1993 | Wuelknitz et al. | |
| 5,320,862 A | 6/1994 | La Tona | |
| 6,294,161 B1 | 9/2001 | Hiramoto et al. | |
| 6,322,838 B1 | 11/2001 | Güntert et al. | |
| 6,375,933 B1 | 4/2002 | Subramanyam et al. | |
| 6,379,652 B1 | 4/2002 | Liu et al. | |
| 6,518,227 B2 | 2/2003 | Woosley | |
| 6,680,289 B1 | 1/2004 | Woo et al. | |
| 6,689,342 B1 | 2/2004 | Pan et al. | |
| 6,733,798 B2 | 5/2004 | Heeg et al. | |
| 6,740,311 B2 | 5/2004 | White, Jr. et al. | |
| 2003/0206874 A1 | 11/2003 | Doyle et al. | |
| 2004/0120902 A1 * | 6/2004 | Wernett et al. | 424/52 |

OTHER PUBLICATIONS

Peppermint oil, www.kvaromatics/mint-products.html, p. 1.*

* cited by examiner

*Primary Examiner* — Brian Gulledge
*Assistant Examiner* — Snigdha Maewall
(74) *Attorney, Agent, or Firm* — Howard C. Lee

(57) ABSTRACT

Toothpowder comprising natural calcium carbonate with a flavor oil coating is derived by agitating a particulated calcium carbonate bed and by spraying a nebula of flavor oil into the bed. The spray rate is controlled to preclude formation of agglomerated particles of the coated natural calcium carbonate.

17 Claims, No Drawings

COATED NATURAL CALCIUM CARBONATE ORAL CARE TOOTHPOWDER COMPOSITION

The present invention relates to toothpowder oral care compositions and methods. In particular, the present invention includes toothpowder compositions and methods for making natural calcium carbonate toothpowder that provide a coating of flavor oil on the natural calcium carbonate particles.

Oral care compositions are used for a wide variety of purposes, including for enhancing personal health, hygiene, and appearance, as well as for preventing or treating a variety of diseases and other conditions in humans and in animals.

The formulation of such compositions presents a number of challenges. They must be pharmaceutically and/or cosmetically acceptable for their intended use. Compositions that contain therapeutic active materials preferably deliver the active at effective levels, avoiding undue chemical degradation. Similarly, compositions containing cosmetically functional materials must deliver the material to the oral cavity at effective levels under the conditions that they are typically used by the consumer.

Moreover, the aesthetic appeal of all such compositions is important, and can have significant effects on consumer acceptance and usage. Aesthetic effects have been acknowledged to play an important role in consumer acceptance of many products. Although such products have met with consumer approval, the art seeks to further improve the aesthetic effects as well as the cosmetic and therapeutic benefits of these products. Indeed, many such compositions known in the art are deficient in one or more attributes. Thus, there is an ongoing need for new oral care compositions, and methods of their use.

One form of oral care composition is a tooth powder. Traditionally, toothpowder has used a combination of precipitated calcium carbonate, natural calcium carbonate, and refined natural calcium carbonate. Flavor oil is added to the precipitated calcium carbonate prior to admixing of the flavor-enhanced precipitated calcium carbonate with the natural calcium carbonate and refined natural calcium carbonate since oil absorption of precipitated calcium carbonate is substantially greater than oil absorption of natural calcium carbonate and/or refined natural calcium carbonate.

However, the effectiveness of toothpowder in providing a pleasant flavor is adversely affected because the precipitated calcium carbonate doesn't fully release flavorant absorbed into it during a normal tooth brushing operation. Furthermore, precipitated calcium carbonate is less cost-effective than natural calcium carbonate in providing the desired abrasive properties of the toothpowder.

SUMMARY

The present invention provides oral care compositions. In somewhat greater detail, the invention is for toothpowder, comprising:

(a) from about 85 to about 100 weight percent particulated natural calcium carbonate where the particulated natural calcium carbonate comprises a set of natural calcium carbonate particles having a set of calcium carbonate surfaces; and (b) flavor oil coating on a majority of calcium carbonate surfaces in the set of natural calcium carbonate surfaces.

In a further aspect, at least 95 percent of individual natural calcium carbonate particles in the set of natural calcium carbonate particles have an independent calcium carbonate particle size from about 1 to about 150 microns, the flavor oil coating on the particulated natural calcium carbonate provides coated particulate, and the flavor oil coating comprises from about 0.1 to about 5 weight percent of the coated particulate.

In yet further aspects, the toothpowder further optionally comprises any of dispersed sodium lauryl sulfate particulate, dispersed saccharin particulate, citric acid, and/or dispersed particulated sodium monofluorophosphate.

In one aspect, a particulate bed of the toothpowder has a volume of at least 125 cubic millimeters and comprises from about 85 to about 98 weight percent natural calcium carbonate, from about 0.38 to about 1.14 weight percent sodium monofluorophosphate, from about 0.5 to about 3.5 weight percent sodium lauryl sulfate, from about 0.02 to about 0.5 weight percent saccharin, from about 0.05 to about 0.4 weight percent citric acid, and from about 0.5 to about 5 weight percent flavor oil.

The invention also provides a method for making toothpowder according to any of the above compositional formulations by agitating a bed of particulated calcium carbonate to provide an agitated bed of not less than 85 weight percent natural calcium carbonate and admixing nebulized flavor oil into the agitated bed to provide coated natural calcium carbonate. The agitated bed of natural calcium carbonate has a volumetric circulation rate and a bed shear rate, and the admixing meters the nebulized flavor oil into the agitated bed at a volumetric rate sufficient, at the volumetric circulation rate and at the bed shear rate, for essentially precluding formation of agglomerated particles of the coated natural calcium carbonate.

In one aspect, the agitating is performed by use of a ribbon blender. In another aspect, flavor oil is nebulized with a spray nozzle to provide the nebulized flavor oil. In another aspect (where the ribbon blender has a housing defining an internal cavity, a spray nozzle is positioned to spray within the internal cavity, and a flavor oil supply is in fluid communication with the spray nozzle) the method further comprises feeding, during the agitating, flavor oil through the spray nozzle from the flavor oil supply to nebulize the flavor oil into the nebulized flavor oil having droplets of from about 5 to about 20 microns.

In one aspect, the agitated bed is kept at a temperature of from about 20 degrees Celsius to about 60 degrees Celsius. It has been discovered that compositions and methods of this invention afford advantages over oral care compositions among known in the art.

Further areas of applicability will become apparent from the detailed description provided hereinafter. It should be understood that the detailed description and specific examples, while indicating embodiments of the invention, are intended for purposes of illustration only and are not intended to limit the scope of the invention.

DESCRIPTION

The following definitions and non-limiting guidelines must be considered in reviewing the description of this invention set forth herein. The headings (such as "Introduction" and "Summary,") and sub-headings (such as "Compositions" and "Methods") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition, unless otherwise specified.

Compositions

The present invention provides toothpowder as oral care compositions and methods for administration or application to, or use with, a human or other animal subject. In overview, a toothpowder oral care composition of from about 85 to about 100 weight percent particulated natural calcium carbonate coated with flavor oil is achieved with careful admixing of nebulized flavor oil into an agitated bed of natural calcium carbonate.

As referred to herein, an "oral care composition" is any composition that is suitable for administration or application to the oral cavity a human or animal subject for enhancing the health, hygiene or appearance of the subject, preferably providing such benefits as: the prevention or treatment of a condition or disorder of the teeth, gums, mucosa or other hard or soft tissue of the oral cavity; the prevention or treatment of a systemic condition or disorder; the provision of sensory, decorative or cosmetic benefits; and combinations thereof. In various preferred embodiments, an oral care composition is not intentionally swallowed, but is rather retained in the oral cavity for a time sufficient to effect the intended utility. Preferably, specific materials and compositions to be used in this invention are, accordingly, pharmaceutically- or cosmetically-acceptable, clinically effective, and/or clinically efficacious. As used herein, such a "pharmaceutically acceptable" or "cosmetically acceptable", "clinically effective", and/or "clinically efficacious" component is one that is suitable for use with humans and/or animals to provide the desired therapeutic, prophylactic, sensory, decorative, or cosmetic benefit without undue adverse side effects (such as toxicity, irritation, and allergic response) commensurate with a reasonable benefit/risk ratio.

Orally Acceptable Carrier

The present invention provides toothpowder compositions comprising an orally acceptable carrier. Such a carrier comprises a material or combination of materials that is safe for use in the compositions of the present invention, commensurate with a reasonable benefit/risk ratio, with which flavor oil and natural calcium carbonate may be intrinsically associated while retaining significant efficacy. In use, the carrier provides an orally acceptable particulate bed. As used herein, an "orally acceptable particulate bed" refers to a quantity of the composition for application to the teeth of a human or other animal subject in a single use. In various embodiments, the bed has a minimum weight of about 1 gram, conforming to a volume of about 0.95 cc., for application to the teeth in a single instance of a tooth brushing operation. In packaged form for consumer purchase, the bed varies from a size of about 10 grams in a sachet up to about 300 grams in a large can. In manufacturing operations, the bed constitutes a normal charge for a mixing system such as a ribbon blender.

Materials among those that are useful in carriers include adhesion agents, surfactants, foam modulators, abrasives, pH modifying agents, humectants, mouth feel agents, sweeteners, colorants, and combinations thereof. It is understood that while general attributes of each of the above categories of materials may differ, there may be some common attributes and any given material may serve multiple purposes within two or more of such categories of materials. Preferably, such carrier materials are selected for compatibility with other ingredients of the composition.

Mouth-feel agents include materials imparting a desirable texture or other feeling during use of the composition. Such agents include dispersed flavorants and sweeteners.

Flavorants among those useful herein include flavor oils of any material or mixture of materials operable to enhance the taste of the composition. Any orally acceptable natural or synthetic flavorant can be used, such as flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc. flavorants, and mixtures thereof. Also encompassed within flavorants herein are ingredients that provide fragrance and/or other sensory effect in the mouth, including cooling or warming effects. Such ingredients include methol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are present in a total amount of about 0.05% to about 5%, optionally in various embodiments from about 0.05 to about 2%, from about 0.1% to about 2.5%, and from about 0.1 to about 0.5%.

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from about 0.005% to about 5%, optionally from about 0.01% to about 1%.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20%, for example about 0.01% to about 10% or about 0.1% to about 5%.

Active Materials

The compositions of the present invention optionally comprise a fluoride ion providing material as an active material, which is operable for the prevention or treatment of a condition or disorder of hard or soft tissue of the oral cavity, the prevention or treatment of a physiological disorder or condition, or to provide a cosmetic benefit. In various embodiments, the active is a "systemic active" which is operable to treat or prevent a disorder that, in whole or in part, is not a disorder of the oral cavity. In various embodiments, the active is an "oral care active" operable to treat or prevent a disorder or provide a cosmetic benefit within the oral cavity (e.g., to the teeth, gingiva or other hard or soft tissue of the oral cavity). Oral care actives among those useful herein include whitening agents, anticaries agents, tartar control agents, antiplaque agents, periodontal actives, abrasives, breath freshening agents, malodour control agents, tooth desensitizers, salivary stimulants, and combinations thereof. It is understood that while general attributes of each of the above categories of actives may differ, there may some common attributes and any given material may serve multiple purposes within two or more of such categories of actives.

Actives useful herein are present in the compositions of the present invention in safe and effective amounts. A "safe and effective" and "clinically efficacious" amount of an active is an amount that is sufficient to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific safe and effective ("clinically efficacious") amount of the active will vary with such factors as the particular condition being treated, the physical condition of the subject, the nature of concurrent therapy (if any), the specific active used, the specific dosage form, the carrier employed, and the desired dosage regimen.

The compositions of the present invention comprise particulated natural calcium carbonate as at least 85 weight percent of the toothpowder where the particulated natural calcium carbonate provides an abrasive useful, for example, as a polishing agent. Any other orally acceptable abrasive is optionally added to the natural calcium carbonate, but type, fineness (particle size) and amount of abrasive should be selected so that tooth enamel is not excessively abraded in normal use of the composition. Suitable additional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

The compositions of the present invention optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

The compositions of the present invention optionally comprise a fluoride ion source useful, for example, as an anticaries agent. Any orally acceptable particulated fluoride ion source can be used, including potassium, sodium and ammonium fluorides and monofluorophosphates, stannous fluoride, indium fluoride, amine fluorides, including olaflur (N'-octadecyltrimethylendiamine-N,N,N'-tris(2-ethanol)-dihydrofluoride), and mixtures thereof. Particulate sodium monofluorophosphate is preferred. One or more fluoride ion sources are optionally present in an amount providing a clinically efficacious amount of fluoride ion, not exceeding 1500 ppm of fluoride ion in any bed quantity of not less than about 1 gram. In one embodiment, from about 0.38 to about 1.14 weight percent sodium monofluorophosphate particulate is dispersed throughout the coated natural calcium carbonate bed of tooth powder.

The compositions of the present invention optionally comprise a saliva stimulating agent, useful for example in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

In one embodiment of a fully formulated exemplary toothpowder, a particulate bed of toothpowder having a volume of at least 125 cubic millimeters has about 85 to about 98 weight percent natural calcium carbonate coated with flavorant, from about 0.38 to about 1.14 weight percent sodium monofluorophosphate particulate, from about 0.5 to about 3.5 weight percent sodium lauryl sulfate, from about 0.02 to about 0.5 weight percent saccharin, from about 0.05 to about 0.4 weight percent citric acid, and from about 0.5 to about 5 weight percent flavor oil as the coating on the calcium carbonate particulate.

Methods of Manufacture

The toothpowder compositions of the present invention are made by methods; these methods include pulverizing (and, optionally, screen filtering) natural calcium carbonate particulate to have independent calcium carbonate particle sizes from about 1 to about 150 microns (preferably from about 6 to about 35 microns, and more preferably from about 6 to about 13 microns) in the individual particles of the natural calcium carbonate particulate. The methods also include admixing of nebulized flavor oil into the orally acceptable natural calcium carbonate particulate in a system such as a ribbon blender. In one embodiment, the orally acceptable natural calcium carbonate particulate is pulverized so that, in a bed having a volume of at least 125 cubic millimeters, at least 99 percent of individual natural calcium carbonate particles in the bed have an independent calcium carbonate particle size from about 1 to about 150 microns (preferably from about 6 to about 35 microns, and more preferably from about 6 to about 13 microns). If optional fluoride ion source particles are admixed into the coated natural calcium carbonate, it is preferred that the fluoride ion source particles are also sized so that at least 99 percent of individual particulate fluoride ion source particles in the set have an independent particulate fluoride ion source particle size from about 1 to about 150 microns (preferably from about 6 to about 35 microns, and more preferably from about 6 to about 13 microns), and any 125 cubic millimeter volumetric portion of the bed has a concentration of not greater than 1500 parts per million of fluoride ion source respective to the natural calcium carbonate.

In one embodiment, a bed of particulated natural calcium carbonate is agitated in a ribbon blender to provide an agitated bed of calcium carbonate, and nebulized flavor oil is admixed into the agitated bed to provide coated natural calcium carbonate. In this regard, the technique of addition is to add the nebulized flavor oil at a volumetric rate that is sufficiently paced (is sufficient for enabling the process to execute in such a manner) so that agglomerated particles of the coated natural calcium carbonate do not develop in the agitated bed of the ribbon blender. In this regard, the agitated bed of natural calcium carbonate has a volumetric circulation rate and a bed shear rate that are essentially specific to the ribbon blender and the particular charge of natural calcium carbonate being agitated. The volumetric circulation rate and the bed shear rate then determine (quantitatively or qualitatively) the appropriate rate for volumetrically metering the nebulized flavor oil into the agitated bed so that formation of agglomerated particles of coated natural calcium carbonate is essentially precluded.

The flavor oil is nebulized (or atomized) to form a preferably very fine spray or fog of flavor oil. The liquid flavorant supplied to the agitated bed of natural calcium carbonate is a substantially uniformly distributed mist or fine spray of particles having a mean average droplet diameter (droplet size) of from about 5 to about 20 microns. In this regard and in one embodiment, the ribbon blender's internal cavity (the space defined within the housing of the ribbon blender) acquires nebulized flavor oil from a spray nozzle positioned to spray within the internal cavity. A flavor oil supply is piped to be in fluid communication with the spray nozzle, and flavor oil is fed, during the agitating of the natural calcium carbonate particulate in the ribbon blender, through the spray nozzle from the flavor oil supply to nebulize the flavor oil into the nebulized flavor oil.

In one embodiment, the agitated bed in the ribbon blender is kept at a temperature of from about 20 degrees Celsius to about 60 degree Celsius during the addition of the flavor oil spray to the agitated bed.

In one embodiment, a uniform dispersion of optional fluoride in the tooth powder and major abrasive is achieved, after adjusting of the particle size distribution of the optional fluoride oral care active particulate (fluoride ion source) to match the major abrasive (coated natural calcium carbonate particulate) particle size is first performed, by adding the fluoride ion source particulate into both ends of the ribbon blender mixer. In this regard, ribbon blenders have a U-shaped horizontal trough (with the U shape of the inner shell being apparent when viewed from the end cross section of the trough in parallel view along the trough axis) and a specially fabricated elongated ribbon agitator positioned to rotate about the trough axis in the generally semi-circular portion of the trough conformant to the lower part of the U. The ribbon agitator has at least one inner helical agitator and at least one outer helical agitator. In operation at least one helical agitator (ribbon) thereby rotates to "drive" material in the leftward (as viewed in trough axial cross section perpendicular to the trough axis) direction of the trough and at least one helical agitator (ribbon) rotates to "drive" material in the (opposite) rightward direction.

The trough (ribbon blender) has two ends (each conforming to the U shape in parallel view along the trough axis). In one embodiment, the abrasive particulate is charged to the ribbon blender, the charged abrasive particulate is then agitated, the flavorant oil is coated onto the natural calcium carbonate, and the blending of fluoride ion source particulate and major abrasive particulate (coated natural calcium carbonate particulate) to fully disperse the oral care active particulate (fluoride ion source) is achieved by continuous addition of the fluoride ion source particulate over a period of time to both of the two ends of the ribbon blender during agitation of the coated abrasive particulate. In this regard, addition at both ends appears to minimize challenges in localized concentration of the fluoride ion source particulate within the toothpowder.

Additional ingredients such as coloring, and/or sweeteners are added at any point during the mixing process, but, in various embodiments, such ingredients are preferably added either last or close to last.

Methods of Use

The present invention provides methods for cleaning a tooth surface using compositions according to the present invention. As referred to herein, "tooth" or "teeth" refers to natural teeth, dentures, dental plates, fillings, caps, crowns, bridges, dental implants, and the like, and any other hard surfaced dental prosthesis either permanently or temporarily fixed within the oral cavity.

Accordingly, the present invention provides methods for cleaning a tooth surface, comprising applying to the surface a safe and effective amount of about 1 gram of aqueously moistened toothpowder and then agitating the aqueously moistened toothpowder against each surface of the tooth with a toothbrush. As referred to herein, "applying" refers to any method by which the toothpowder is placed in contact with the tooth surface.

In various embodiments, compositions of the present invention are also used for the treatment or prevention of disorders in the oral cavity, including cavity prevention, whitening, plaque prevention or reduction, gingivitis prevention or reduction, tartar control, sensitivity prevention or reduction, breath malodor prevention or reduction, and stain prevention. Compositions of the present invention may also be used for the treatment or prevention of systemic disorders, such as the improvement of overall systemic health characterized by a reduction in risk of development of systemic diseases, such as cardiovascular disease, stroke, diabetes, severe respiratory infection, premature and low birth weight infants (including associated post-partum dysfunction in neurologic/developmental function), and associated increased risk of mortality. Such methods include those disclosed in U.S. Patent Publication 2003/0206874, Doyle et al., published Nov. 6, 2003.

The present invention is further illustrated through the following non-limiting examples.

EXAMPLE 1

A 100 kg bed of natural calcium carbonate is pulverized and screened to provide natural calcium carbonate having a particle diameter of less than 150 microns. The bed is agitated in a ribbon blender and atomized particles of flavor spray are added to the bed through a 1 mm nozzle. Particle sizes of the flavor spray droplets are determined to be from 5-20 micron. The flavor mist is added over a period of 15 minutes at a rate at of 0.15 kg/min to provide 2.3 kg 'neat' flavorant coating of undiluted spray on the natural calcium particulates of the 100 kg batch.

EXAMPLE 2

A 100 kg bed of intermixed natural calcium carbonate precipitated calcium carbonate is pulverized and screened to provide calcium carbonate having a particle diameter of less than 150 microns. The bed is agitated in a ribbon blender and atomized particles of flavor spray are added to the bed through a 1 mm nozzle. Particle sizes of the flavor spray droplets are determined to be from 5-20 micron. The flavor mist is added over a period of 15 minutes at a rate at of 0.15 kg/min to provide 2.3 kg 'neat' flavorant coating of undiluted spray on the calcium particulates of the 100 kg batch.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

What is claimed is:

1. Toothpowder, comprising: (a) from about 85 to about 100 weight percent particulated natural calcium carbonate wherein said particulated natural calcium carbonate comprises natural calcium carbonate particles having calcium carbonate surfaces; and (b) flavor oil coating on a majority of calcium carbonate surfaces on said natural calcium carbonate surfaces.

2. The toothpowder of claim 1 wherein at least 95 percent of said natural calcium carbonate particles have a particle size from about 1 to about 150 microns, said flavor oil coating on said particulated natural calcium carbonate provides coated particulate, and said flavor oil coating comprises from about 0.1 to about 5 weight percent of said coated particulate.

3. The toothpowder of claim 1 further comprising dispersed sodium lauryl sulfate particulate.

4. The toothpowder of claim 1 further comprising dispersed saccharin particulate.

5. The toothpowder of claim 1 further comprising citric acid.

6. The toothpowder of claim 1 further comprising clinically efficacious particulated sodium monofluorophosphate.

7. The toothpowder of claim 1 wherein a particulate bed of said toothpowder having a volume of at least 125 cubic millimeters comprises from about 85 to about 98 weight percent natural calcium carbonate, from about 0.38 to about 1.14 weight percent sodium monofluorophosphate, from about 0.5 to about 3.5 weight percent sodium lauryl sulfate, from about 0.02 to about 0.5 weight percent saccharin, from about 0.05 to about 0.4 weight percent citric acid, and from about 0.5 to about 5 weight percent flavor oil.

8. A method for making toothpowder, of claim 1 comprising: (a) agitating a bed of particulated calcium carbonate to provide an agitated bed of calcium carbonate, said particulated calcium carbonate comprising not less than 85 weight percent natural calcium carbonate; and (b) admixing nebulized flavor oil into said agitated bed to provide coated natural calcium carbonate; (c) wherein said agitated bed of natural calcium carbonate has a volumetric circulation rate and a bed shear rate, and said admixing meters said nebulized flavor oil into said agitated bed at a volumetric rate sufficient, at said volumetric circulation rate and at said bed shear rate, for essentially precluding formation of agglomerated particles of said coated natural calcium carbonate.

9. The method of claim 8 further comprising dispersing sodium lauryl sulfate particulate into said toothpowder.

10. The method of claim 8 further comprising dispersing saccharin particulate into said toothpowder.

11. The method of claim 8 further comprising dispersing citric acid into said toothpowder.

12. The method of claim 8 wherein said agitating is performed by use of a ribbon blender.

13. The method of claim 8 further comprising nebulizing flavor oil with a spray nozzle to provide said nebulized flavor oil.

14. The method of claim 12 wherein said ribbon blender has a housing defining an internal cavity, a spray nozzle positioned to spray within said internal cavity, and a flavor oil supply in fluid communication with said spray nozzle, said method further comprising feeding, during said agitating, flavor oil through said spray nozzle from said flavor oil supply to nebulize said flavor oil into said nebulized flavor oil.

15. The method of claim 12 wherein said agitated bed is at a temperature of from about 20 degrees Celsius to about 60 degree Celsius.

16. The method of claim 14 wherein said nebulized flavor oil has a droplet size of from about 5 to about 20 microns.

17. Toothpowder made by a process according to the method of claim 8.

* * * * *